United States Patent
Brockmann

(10) Patent No.: US 12,096,975 B2
(45) Date of Patent: Sep. 24, 2024

(54) RESECTOSCOPE HAVING AN ELECTRODE INSTRUMENT IN THE OUTER SHAFT

(71) Applicant: OLYMPUS WINTER & IBE GMBH, Hamburg (DE)

(72) Inventor: Christian Brockmann, Hollenstedt (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 615 days.

(21) Appl. No.: 17/297,943

(22) PCT Filed: Nov. 25, 2019

(86) PCT No.: PCT/EP2019/082476
§ 371 (c)(1),
(2) Date: May 27, 2021

(87) PCT Pub. No.: WO2020/109257
PCT Pub. Date: Jun. 4, 2020

(65) Prior Publication Data
US 2022/0047321 A1    Feb. 17, 2022

(30) Foreign Application Priority Data
Nov. 27, 2018  (DE) .................. 10 2018 129 904.4

(51) Int. Cl.
*A61B 18/14*   (2006.01)
*A61B 1/00*    (2006.01)
(Continued)

(52) U.S. Cl.
CPC ........ *A61B 18/149* (2013.01); *A61B 1/00087* (2013.01); *A61B 1/00119* (2013.01); *A61B 1/002* (2013.01); *A61B 2018/00982* (2013.01)

(58) Field of Classification Search
USPC .................................. 600/105, 135
See application file for complete search history.

(56) References Cited

U.S. PATENT DOCUMENTS 3,850,175 A * 11/1974 Iglesias .................... A61B 1/12
                                                         600/105
3,900,022 A   8/1975  Widran
(Continued)

FOREIGN PATENT DOCUMENTS

DE         10310614 B4    10/2007
DE    10 2015 014 254 A1   5/2017
(Continued)

OTHER PUBLICATIONS

Apr. 1, 2020 International Search Report issued in International Patent Application No. PCT/EP2019/082476.

*Primary Examiner* — John P Leubecker
(74) *Attorney, Agent, or Firm* — Oliff PLC

(57) ABSTRACT

A resectoscope for endoscopic surgery, having a tubular shaft which includes an elongated sheath tube, and an irrigation tube arranged in the sheath tube for supplying irrigation fluid, as well as a rod-shaped lens and an electrode instrument, characterized in that the lens and the electrode instrument are arranged between the outer wall of the irrigation tube and the inner wall of the sheath tube. In addition, an electrosurgical system including the resectoscope and an irrigation fluid supply device.

9 Claims, 3 Drawing Sheets

(51) Int. Cl.
    *A61B 1/002*     (2006.01)
    *A61B 18/00*     (2006.01)

(56) References Cited

U.S. PATENT DOCUMENTS

| | | | |
|---|---|---|---|
| 4,423,727 | A | 1/1984 | Widran et al. |
| 4,950,278 | A * | 8/1990 | Sachse ............ A61B 1/12 |
| | | | 600/105 |
| 5,112,330 | A | 5/1992 | Nishigaki et al. |
| 5,807,240 | A | 9/1998 | Muller et al. |
| 6,086,584 | A * | 7/2000 | Miller ............ A61B 18/08 |
| | | | 606/49 |
| 6,358,200 | B1 | 3/2002 | Grossi |
| 2006/0015007 | A1 * | 1/2006 | Aue ............ A61B 18/149 |
| | | | 600/105 |
| 2007/0270788 | A1 * | 11/2007 | Nahen ............ A61B 1/015 |
| | | | 606/15 |
| 2008/0045859 | A1 * | 2/2008 | Fritsch ............ A61B 18/148 |
| | | | 600/567 |
| 2011/0160715 | A1 * | 6/2011 | Ostrovsky ............ A61B 1/015 |
| | | | 606/28 |
| 2011/0295066 | A1 * | 12/2011 | Fan ............ A61B 1/00128 |
| | | | 600/156 |
| 2017/0055811 | A1 | 3/2017 | Germain et al. |
| 2017/0056094 | A1 | 3/2017 | Sartor et al. |
| 2017/0340192 | A1 * | 11/2017 | Begg ............ A61B 1/3132 |

FOREIGN PATENT DOCUMENTS

| | | |
|---|---|---|
| DE | 10 2018 114 448 A1 | 12/2019 |
| WO | 2016185102 A1 | 11/2016 |

* cited by examiner

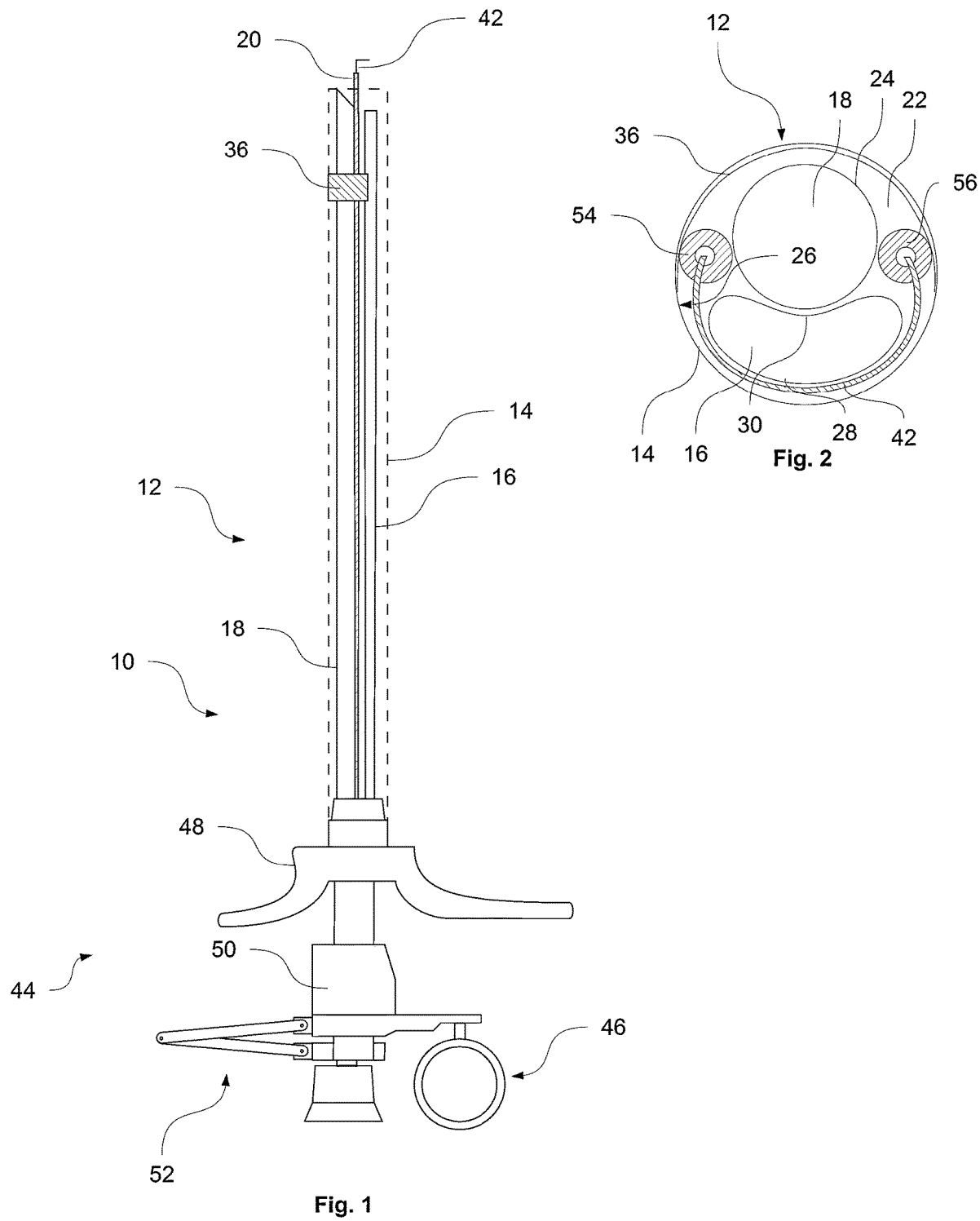

RESECTOSCOPE HAVING AN ELECTRODE INSTRUMENT IN THE OUTER SHAFT

BACKGROUND

The invention relates to a resectoscope for endoscopic surgery, and to a an electrosurgical system that includes the resectoscope.

Resectoscopes of the generic type are used primarily in urology for surgical work in the bladder and urethra. They are usually used for resection and vaporization of tissue, for example tissue in the lower urinary tract. For this purpose, the resectoscopes comprise a longitudinally displaceable electrosurgical passage instrument, the distal end of which, after the resectoscope has been inserted, can be pushed out of the distal end of the shaft tube of the resectoscope. The electrosurgical passage instrument can comprise an electrosurgical electrode at its distal working end, for example in the form of a loop or plasma button. Such instruments are, for example, the OES PRO resectoscopes (Olympus) or other resectoscopes with continuous irrigation according to Iglesias.

The instruments contain a lens that can be used to monitor the surgical site during the operation. In order to expand the anatomy in the field of vision, to wash away local bleeding that occurs during the procedure, and to protect the tissue from heat damage caused by the high-frequency electrosurgical application, the resectoscopes are equipped with an irrigation device that permanently irrigates the tissue in front of the distal end of the shaft. In conventional irrigation devices, irrigation fluid is continuously passed through an inner shaft and exits at the distal end of the resectoscope. The return flow of the irrigation fluid usually takes place through a gap between the inner and outer shaft. For this purpose, the outer shaft has numerous irrigation bores for taking up liquid.

In current resectoscopes, both the electrosurgical passage instrument and the rod-shaped lens run through the inner tube, which is also used for the supply of irrigation fluid. It has been shown that such a system is not optimal for guiding the irrigation flow, since, among other things, the electrode is located directly in the inflow channel and can thus generate turbulence in the irrigation fluid immediately before it emerges from the shaft. Such turbulence can severely obstruct the view of the operating area. In addition, in the annular gap between the inner tube and the sheath tube (outer tube), which is usually used for the return flow, only low return flow velocities can develop due to friction effects of the wall.

There is therefore a need for systems in which undesired turbulence in the irrigation fluid inflow is avoided or reduced, and in which the return flow velocity is variable.

DESCRIPTION

These objects are achieved by embodiments of a resectoscope and an electrosurgical system according to the invention. In particular, the objects are achieved by guiding the electrode instrument and the rod-shaped lens parallel to—that is, outside of—the inner tube (irrigation tube) used for the supply of irrigation fluid. The two passage instruments (electrode instrument and lens) are therefore no longer guided within the inner tube. In this way, turbulence is avoided. In addition, the entire remaining interior space of the outer tube (sheath tube) can be used to route the contaminated irrigation fluid out of the patient's body.

In a first aspect, the invention thus relates to a resectoscope for endoscopic surgery, having a tubular shaft which comprises an elongated sheath tube and an irrigation tube arranged in the sheath tube for supplying irrigation fluid, as well as a rod-shaped lens and an electrode instrument, characterized in that the lens and the electrode instrument are arranged between the outer wall of the irrigation tube and the inner wall of the sheath tube. According to the invention, an arrangement "between" the outer wall and the inner wall means that no further separating elements are arranged between the named elements. In particular, the electrode instrument and the lens are only enclosed by the sheath tube and not by a further inner tube.

The resectoscope according to the invention is suitable for various procedures in endoscopic surgery, in particular in electrosurgical surgery. For example, the resectoscope can be used for prostate resection, in which particularly heavy blood loss can occur. At the same time, the resectoscope can also be used for a variety of other operations, such as bladder resections.

In a conventional embodiment, the resectoscope has a tubular shaft. In addition to this shaft part, the resectoscope includes a handle system for holding and operating the resectoscope, which handle system usually consists of two handle parts.

The endoscope shaft comprises an elongated sheath tube. An irrigation tube (inner tube), a rod-shaped lens, and an electrode instrument (electrosurgical passage instrument) are arranged inside the sheath tube. The lens and electrode instrument are arranged radially adjacent to the irrigation tube inside the sheath tube. In other words, the irrigation tube, lens and electrode instrument pass through the sheath tube next to each other. It is particularly intended that the irrigation tube is arranged below a transverse plane of the resectoscope. In a spatial orientation, a resectoscope can be divided into different regions by a transverse plane that cuts the shaft tube in both the longitudinal direction and horizontally, and a sagittal plane perpendicular to the transverse plane, wherein the longitudinal axis of a shaft tube lies both in the sagittal plane and in the transverse plane. The transverse plane passes through the shaft tube transversely and, in a position of use of the resectoscope, in a horizontal orientation. The sagittal plane passes through the shaft tube perpendicularly and, in a position of use of the resectoscope, in a vertical orientation. The sagittal plane can in particular be parallel to a movement plane defined by a relative movement of handle parts mounted on the resectoscope such that they can pivot with respect to each other, for example for the actuation of a slide of the resectoscope. In a particularly preferred embodiment, the irrigation tube is arranged in a 6-o'clock position below the lens, such that the longitudinal axes of the irrigation tube and the lens lie in the sagittal plane of the resectoscope.

According to the invention, as a result of this arrangement, the lens and the electrode instrument are arranged in the space between the outer wall of the irrigation tube and the inner wall of the sheath tube. However, this space is not completely filled by the lens and the electrode instrument. As such, it can also be used for the return flow of irrigation fluid in the proximal direction. The part of the space provided for the return flow can deliberately be larger than usual in order to limit the return flow speed and to increase the speed difference between the inflow and outflow. In the proximal area of the resectoscope, the volume flow of the outflow can also be reduced or slowed down, for example by means of a constriction. According to the invention, the inflow speed is preferably greater than the outflow speed. In this way, among other things, a direct return flow of the irrigation fluid is prevented.

According to the invention, the irrigation tube (inner tube) arranged in the sheath tube is used to supply irrigation fluid. By introducing an irrigation fluid through the irrigation tube into the interior of the body during a medical procedure, it is ensured that the medical staff has a clear view of the treatment area via the lens during the treatment. With this irrigation fluid, pieces of tissue that are released during the resectoscopic procedure can be flushed away, for example. The irrigation fluid also serves to remove cloudiness, caused for example by blood, from the field of view of the lens. The irrigation fluid is fed to the inside of the body via the irrigation tube, while the contaminated irrigation fluid preferably flows out through the space between the inner wall of the sheath tube and the outer wall of the irrigation tube. According to the invention, the irrigation tube is therefore designed in such a way that irrigation fluid and/or body fluids can flow through it, preferably in the distal direction.

For good viewing conditions during the operation, it is essential that the irrigation fluid forms a laminar flow when it enters the body cavity, which is at least almost parallel to a longitudinal axis of the shaft or an optical axis of the lens and allows visual control of the extended electrode. As soon as the irrigation fluid does not flow in a laminar, or even turbulent, manner, the view through the lens can become so poor that an operation cannot be carried out. According to the invention, it can be provided for this purpose that the irrigation tube has a nozzle in its distal end region, by means of which a fluid flow flowing in the distal direction can be directed and/or accelerated. The nozzle can be formed by a narrowing of the irrigation tube in its distal end region or by a separate nozzle part which is arranged at the distal end of the irrigation tube. The nozzle accelerates the irrigation medium and can direct it into the center of the field of vision.

While a nozzle at the distal end of the irrigation tube is the preferred variant according to the invention in order to achieve a flow free of turbulence, it is also conceivable within the scope of the invention to achieve a similar positive effect by means of a diffuser. In an alternative embodiment, the irrigation tube can therefore have a diffuser in its distal end region.

In order to fit the irrigation tube into the sheath tube in a space-saving manner in addition to the lens, it is preferred that the irrigation tube has a cross section with a convexly curved portion and a concavely curved portion, that is, a cross section in the shape of a sickle. The sickle shape preferably has rounded corners or points. The concavely curved portion—the interior of the sickle shape—preferably adjoins the lens at least in portions thereof. The convexly curved portion preferably adjoins the inner wall of the sheath tube.

In order to further reduce the risk of turbulence in the inflow of the irrigation fluid, the irrigation tube has, over the longest possible portion thereof before the distal end, or before the nozzle or the diffuser in the distal end region if the irrigation tube includes such a feature, a cross section with a constant shape and size. For example, it is preferred that the irrigation tube has a cross section that is constant in size and shape over at least 60%, preferably at least 70%, more preferably at least 80%, of the length of the resectoscope shaft. The cross section is preferably constant, in particular in the distal 60%, or 70%, or 80%, of the shaft, with the exception of a potentially present nozzle or a potentially present diffuser.

The freedom from turbulence is further ensured according to the invention by the fact that no passage instruments, in particular no electrode instrument and no lens, are arranged inside the irrigation tube. In conventional resectoscopes, the arrangement of these instruments in the irrigation flow regularly leads to disruptive turbulence in the irrigation flow.

As described elsewhere, a lens and an electrode instrument are arranged in the sheath tube, in addition to the irrigation tube. Suitable electrode instruments for this arrangement are known to those skilled in the art. The electrode instrument generally has an elongated instrument shaft and at least one electrode arranged on the distal end region. The electrode can be designed, for example, as a plasma button, cutting loop or another electrosurgical cutting tool, a cutting loop being preferred. The electrode instrument is preferably a bipolar instrument. However, it is also conceivable to use a monopolar electrode instrument in the resectoscope according to the invention.

The electrode instrument can have two fork tubes. Such a structure is known for many electrode instruments, in particular bipolar instruments with, for example, a cutting loop at the distal end. These fork tubes usually run relatively close to each other in the proximal and central shaft area of the electrode instrument and diverge only in the distal end area of the electrode instrument, such that the distal ends of the fork tubes can accommodate an electrode, for example in the form of a loop electrode or a plasma button, between them. In order, according to the invention, to facilitate the arrangement of the electrode instrument in the space between the sheath tube and the irrigation tube, it can be provided that the fork tubes of the electrode instrument only converge in the proximal end region of the electrode instrument, or not at all. This also maximizes the space available for the irrigation tube. The distance between the fork tubes is therefore, according to the invention, preferably constant over at least 60%, preferably at least 70%, more preferably at least 80% of the shaft of the electrode instrument, from the distal end of the electrode instrument. The fork tubes of the electrode instrument therefore have a straight course up to the transporter of the resectoscope (and parallel to each other), such that the space remaining for the irrigation tube is maximized and obstructions for the liquid outflow are avoided. This design of the fork tubes has the additional advantage of saving assembly costs.

The fork tubes of the electrode instrument, e.g. of an electrode instrument with two fork tubes, preferably run along the inner wall of the sheath tube, it being particularly preferred that the lens is arranged between the two fork tubes of an electrode instrument. In this way, a particularly large amount of space is created for the irrigation tube in the interior of the sheath tube. The two fork tubes of the exemplary electrode instrument can be arranged, for example, between the 9- and 10-o'clock positions and between the 2- and 3-o'clock positions.

The electrode instrument used according to the invention can have one or more holding elements for radial support. This prevents undesired lateral displacement of the electrode during an operation. At the same time, the electrode instrument can be displaced in the axial direction. For example, the electrode which is arranged at the distal end of the electrode instrument can be used to remove tissue. The axial displaceability of the electrode instrument is not impaired by the holding elements.

The holding element or elements can connect the electrode instrument to one of the other elements of the shaft in a radially supporting manner, for example to the lens, the irrigation tube or the sheath tube. In this case, "connecting"

means that each of the holding elements adjoins the given element radially, but can still be displaced relative to the element in the axial direction. The holding element or elements can, for example, adjoin the outer wall of the rod-shaped lens. In an alternative and preferred embodiment, the holding element or elements adjoin the inner wall of the sheath tube. For this purpose, the holding elements preferably have a partially circular cross section. Due to the partially circular cross section, the holding element or elements are complementary in shape to the adjoining element. The holding element or elements, preferably two holding elements, for example, can enclose the lens on a portion of its shaft part in a partially circular shape.

Alternatively, the holding element or elements, preferably one holding element, can run along the inner wall of the sheath tube in the shape of a part of a circle over a portion of the sheath tube. In this case, for example, a holding element can be designed in such a way that it runs along the inner wall of the sheath tube from one fork tube to the other fork tube, and connects the fork tubes to each other in a stabilizing manner, and at the same time supports them radially against the inner wall. The holding element can be arranged between the given fork tube and the inner wall of the sheath tube.

The sheath tube can have an insulating tip at its distal end region. This prevents short circuits between the electrode and more proximally arranged, electrically conductive elements of the resectoscope, such as the irrigation tube. Suitable materials for forming such insulating tips are known to those skilled in the art. For example, the insulating tip can be made of ceramic, plastic or glass. While it is customary and also conceivable within the scope of the invention to design the insulating tip with a beak shape, it is preferred according to the invention that the insulating tip has a constant length in the distal direction along its entire circumference.

The lens of the present resectoscope arranged in the shaft is a rod-shaped lens which in turn has a shaft region that runs through the resectoscope shaft. The lens enables the user to visually monitor the site of the operation and the electrosurgical operation performed. The lens can comprise a lens-based optics system or a fiber optics. In its proximal end area, the lens includes an ocular or a connection to a camera head. At its distal end, the lens is usually protected by a protective glass that can also act as a filter. The lens can be an angled lens to ensure a particularly good view of the surgical site.

In a second aspect, the invention relates to an electrosurgical system which comprises a resectoscope according to the invention, and to an irrigation fluid supply device which is connected to the irrigation tube of the resectoscope. The connection to the irrigation tube ensures that irrigation fluid can flow from the irrigation fluid supply device in the distal direction through the irrigation tube. An irrigation fluid supply device can thus be assigned to the proximal end of the resectoscope or of the shaft, in particular of the irrigation tube. The irrigation fluid supply device is able to direct the irrigation fluid into the interior of the body at a predeterminable pressure. For this purpose, the irrigation fluid supply device can, for example, work exclusively with hydrostatic pressure, that is to say it can be equipped with a fluid reservoir which is arranged above the resectoscope. Alternatively or additionally, the irrigation fluid supply device can comprise a pump, by means of which the irrigation fluid can be pumped through the irrigation tube into the interior of the body.

As a rule, the excess liquid will spontaneously flow out through the space between the irrigation tube and the sheath tube. But it is also possible to ensure the drainage by applying a slight negative pressure. For this purpose, the electrosurgical system can further comprise an irrigation fluid drainage device.

BRIEF DESCRIPTION OF THE FIGURES

Exemplary embodiments of the invention are shown schematically in the drawings, wherein:

FIG. 1 is a schematic, lateral sectional view of a resectoscope according to the invention;

FIG. 2 is a frontal view of the resectoscope shaft from the distal direction, only shaft elements of the resectoscope being shown;

EXEMPLARY EMBODIMENTS

Figure 3:
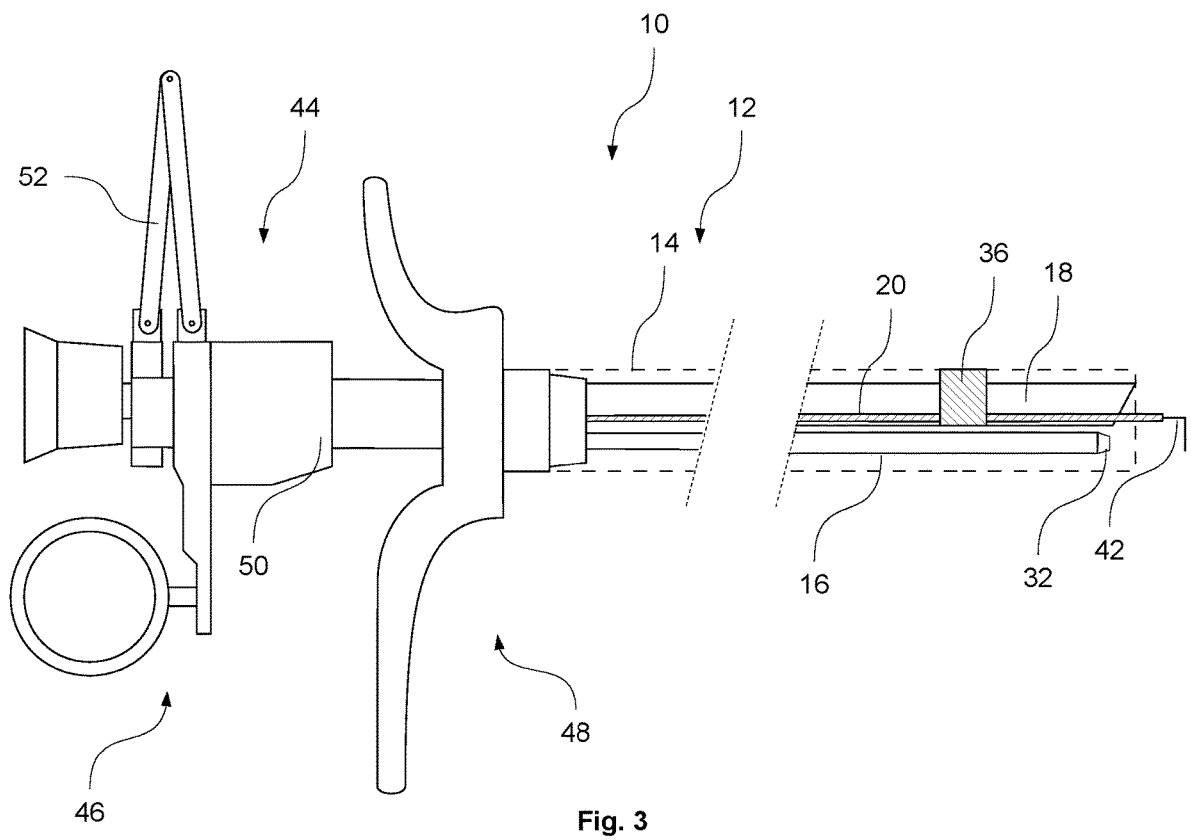
FIG. 3 is a schematic, lateral sectional view of a resectoscope according to the invention, the irrigation tube of which has a nozzle at its distal end.

Further advantages, characteristics and features of the present invention will become apparent in the following detailed description of exemplary embodiments with reference to the accompanying drawings. However, the invention is not restricted to these exemplary embodiments.

FIG. 1 shows a sectional illustration of a resectoscope 10 according to the invention. FIG. 2 shows a frontal view of the resectoscope shaft 12 from the distal direction, only shaft elements of the resectoscope 10 from FIG. 1 being shown, and no elements of the handle 44 being shown. In the usual design, the resectoscope 10 comprises a handle 44 and a shaft 12. The handle 44 is designed to allow holding the resectoscope 10 in one hand and to allow preferably one-handed actuation of the passage instruments extending through the shaft 12.

The resectoscope 10 shown has a passive transporter, in which the slide 50 is displaced in the distal direction against the distal, first handle part 48 by a relative movement of the handle parts 46 and 48 arranged proximally from the resectoscope shaft on the handle 12 against a spring force applied by a spring bridge 52. When the slide 50 is displaced in the distal direction against the handle part 48, the electrode instrument 20 is displaced in a positively guided manner in the distal direction in a manner not shown. When the handle parts 46, 48 are relieved, the spring force generated by the spring bridge 52 forces the slide 50 back into its rest position, the electrode instrument 20 being pulled in the proximal direction. When the slide 50 is moved back, an electrosurgical procedure with the electrode instrument 20 can be carried out without manual force from the surgeon, that is to say, passively.

The shaft 12 of the resectoscope 10 comprises a sheath tube 14, in the interior of which a plurality of elongate passage instruments run, in particular the elongated lens 18, the electrode instrument 20 and the irrigation tube 16. It can be seen in FIGS. 1 and 2 that no further passage instruments run inside the irrigation tube 16. In particular, the electrode instrument 20 and the lens 18 are arranged next to the irrigation tube 16 in the sheath tube 14. For stabilization, the electrode instrument 20 is secured against radial displacement by a holding element 36. The holding element 36 has a partially circular cross section which, in the present instrument, rests against the inner wall 26 of the sheath tube 14 approximately along half the inner circumference of the inner wall 26. The cross section of the holding element 36 is thus approximately semicircular in the present case, as can be seen in FIG. 2. In other words, the holding element 36 is partially complementary in shape to the inner wall 26 of the sheath tube 14. As a result, the holding element 36 can be displaced in the axial direction inside the sheath tube 14 while it is supported radially.

The holding element 36 connects the two fork tubes 54, 56 of the electrode instrument to each other along the inner circumference of the sheath tube 14. The connection between the holding element 36 and the two fork tubes 54, 56 can be established in a conventional manner, such as by laser beam welding. Alternatively, the fork tubes 54, 56 and the holding element 36 can also be produced from one piece.

At its distal end, the electrode instrument 20 has an electrode which, in the present case, is designed as a loop electrode 42 or cutting loop. The instrument is designed as a bipolar instrument and is provided with a counter electrode (not shown). By means of the loop electrode 42, the medical specialist is able to ablate tissue from the surgical site during a surgical procedure.

The irrigation tube 16 has a cross section with a convexly curved portion 28 and a concavely curved portion 30, that is, a cross section in the shape of a sickle with rounded tips. The concavely curved portion 30—the interior of the sickle shape—adjoins the shaft of the lens 18 over the length of the shaft 12. The convexly curved portion 28 adjoins the inner wall 26 of the sheath tube 14. In this way, the available interior space of the sheath tube 14 is used in a manner which is as space-saving as possible, and the internal volume of the irrigation tube 16 is maximized. Irrigation fluid can be conveyed to the surgical site in the distal direction through the irrigation tube 16. The return flow of the contaminated irrigation fluid takes place through the empty space 22 which remains inside the sheath tube 14 next to the passage instruments arranged there, that is, the space 22 which remains in addition to the lens 18, the irrigation tube 16 and the electrode instrument 20.

Figure 4:
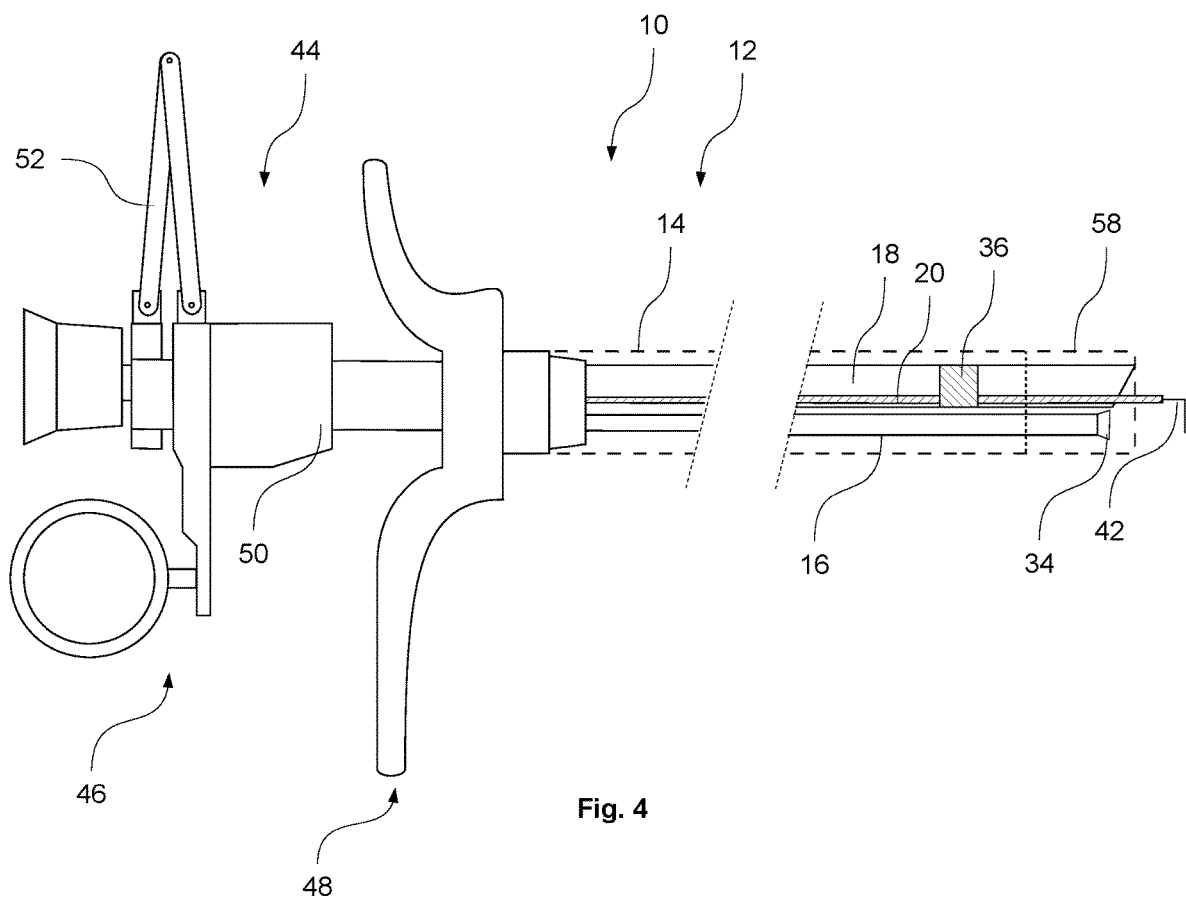
FIG. 4 is a schematic, lateral sectional view of an alternative embodiment of a resectoscope according to the invention, the irrigation tube of which has a diffuser at its distal end.

FIGS. 3 and 4 show two different design variants of the resectoscope shown in FIGS. 1 and 2. In addition to the elements described above, the resectoscope 10 shown in FIG. 3 has a nozzle 32 at the distal end of the irrigation tube 16. The fluid flow flowing in the distal direction can be directed to the surgical site by means of the nozzle 32. In some embodiments, the direction in which the nozzle 32 directs the flow of liquid can be manually or automatically adjustable. In this way, the medical professional can set the direction of the fluid flow during the operation and change it if necessary. In addition, the nozzle 32 has an accelerating effect on the flow of liquid, such that a direct return flow of the irrigation fluid is prevented.

In the alternative embodiment shown in FIG. 4, the irrigation tube 16 has a diffuser 34 at its distal end. By means of the diffuser 34, the fluid flow flowing in the distal direction can be directed and the speed of the fluid flow can be reduced. A diffuser 34 can be useful, for example, in procedures that result in only minor bleeding. Due to the decelerated flow of liquid, the procedure with this embodiment is particularly gentle.

In addition, the resectoscope 10 in FIG. 4 has, as an electrically insulating element at the tip of the sheath tube 14, an insulating tip 58 which is designed as a ceramic tip. A short circuit between the loop electrode 42 and the distal end of the irrigation tube 16 and other elements is prevented in this way.

Finally, the resectoscope 10 shown in FIG. 4 has an electrode instrument 20 with holding elements 36 which differ from that shown in FIGS. 1 to 3. The electrode instrument 20 shown here has two holding elements 36, only one of which can be seen in FIG. 4. The holding elements 36 do not support the electrode instrument 20 on the inner wall 26 of the sheath tube 14, but rather on the outer wall 24 of the lens 18. The cross section of the two holding elements 36 also has a partially circular cross section [sic.], which, however, is smaller than the approximately semi-circular cross section shown in FIG. 2. The holding elements 36 adjoin the outer wall 24 of the lens 18 in a complementary manner, and can be displaced parallel to the lens 18, together with the rest of the electrode instrument 20—that is, in the axial direction.

Figure 5:
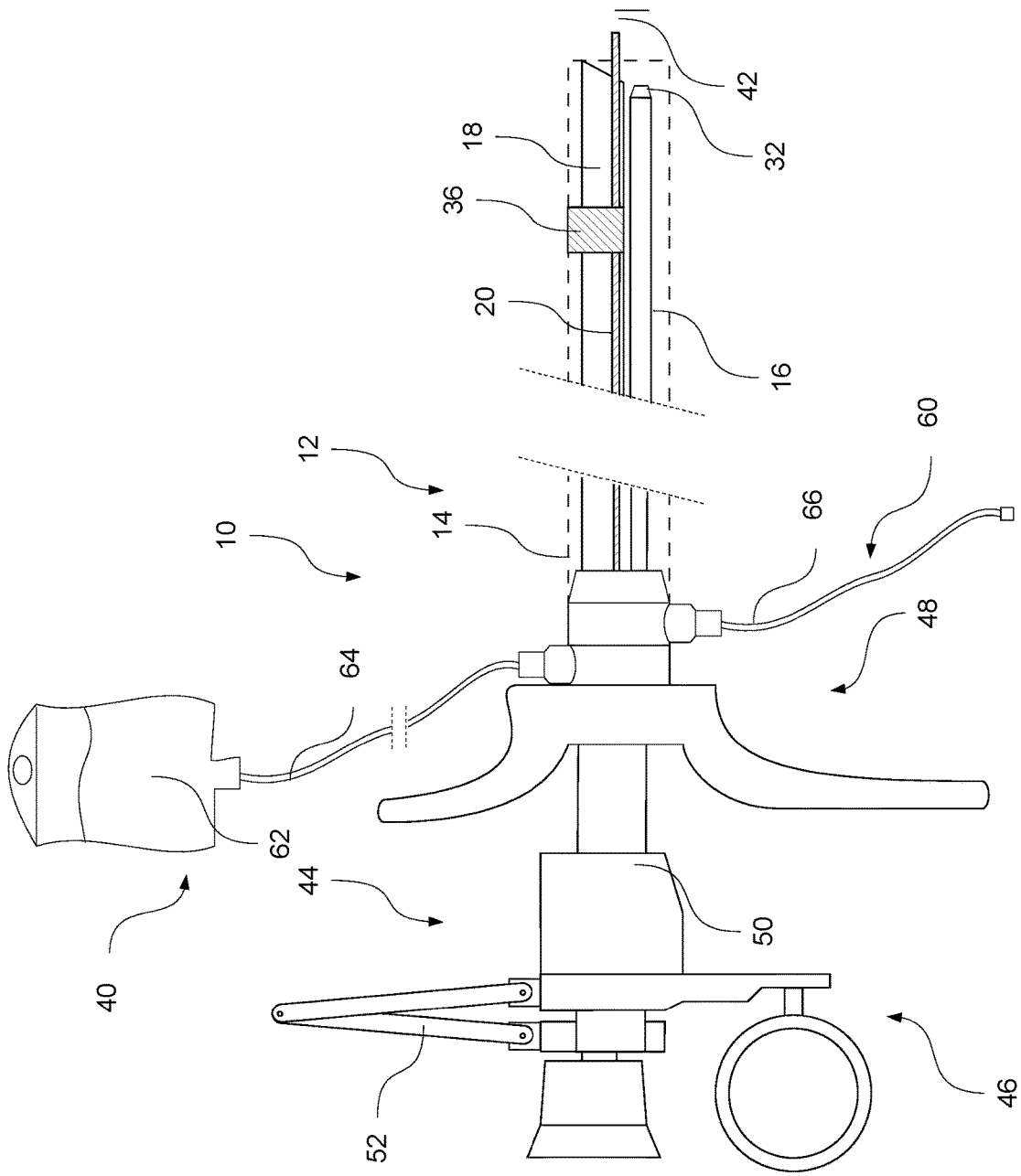
FIG. 5 is a schematic, lateral sectional view of an electrosurgical system according to the invention, which has an irrigation fluid supply device.

FIG. 5 shows a schematic, lateral sectional illustration of an electrosurgical system according to the invention, which has an irrigation fluid supply device 40. In the embodiment shown, the irrigation fluid supply device 40 comprises a fluid reservoir 62 and a hose 64 through which the irrigation fluid can flow into the irrigation tube 16 of the resectoscope 10. In the embodiment shown, the irrigation fluid flows into the irrigation tube as a result of the hydrostatic pressure of the fluid in the fluid reservoir 62. By changing the height of the fluid reservoir 62 in relation to the resectoscope 10, the speed of the irrigation fluid can be adjusted. Once the operation site is reached, the irrigation fluid can flow out again through the space 22 between the inner wall 26 of the sheath tube 14 and the passage instruments arranged therein. In the present case, the irrigation fluid drainage device 60 therefore comprises a hose 66 through which the liquid can flow off.

Although the present invention has been described in detail with reference to the exemplary embodiments, it is obvious to the person skilled in the art that the invention is not restricted to these exemplary embodiments, but rather that modifications are possible in such a way that individual features may be omitted or other combinations of the individual features presented may be realized, provided the scope of protection of the appended claims is not exceeded. The present disclosure includes all combinations of the individual features presented.

The invention claimed is:

1. A resectoscope for endoscopic surgery, comprising:
   a tubular shaft which has an elongated sheath tube, and an inner tube or irrigation tube arranged in the sheath tube for supply of irrigation fluid, as well as a rod-shaped lens and an electrode instrument,
   wherein the lens and the electrode instrument are arranged between the outer wall of the inner tube or irrigation tube and the inner wall of the sheath tube,
   wherein the irrigation fluid supplied through the irrigation tube into a body of a patient can be conveyed back out of the body through the sheath tube, and wherein the irrigation tube has a cross section with a convexly curved portion and a concavely curved portion, and
   wherein the irrigation tube has a nozzle in its distal end region, the nozzle being configured such that a fluid flow flowing in the distal direction is directed and accelerated.

2. The resectoscope according to claim 1, wherein the convexly curved portion adjoins the inner wall of the sheath tube.

3. The resectoscope according to claim 1, wherein the irrigation tube has a diffuser in its distal end region.

4. The resectoscope according to claim 1, wherein the electrode instrument has one or more holding elements for radial support.

5. The resectoscope according to claim 4, wherein the holding element or elements adjoin the inner wall of the sheath tube.

6. The resectoscope according to claim 4, wherein the holding element or elements adjoin the outer wall of the rod-shaped lens.

7. The resectoscope according to claim 1, wherein the irrigation tube has a cross section that is constant in size and shape over at least 60% of the length of the shaft.

8. The resectoscope according to claim 1, wherein no passage instruments are arranged within the irrigation tube.

9. An electrosurgical system, comprising a resectoscope according to claim 1 and an irrigation fluid supply device which is connected to the irrigation tube of the resectoscope.

* * * * *